(12) United States Patent
Moss

(10) Patent No.: US 7,357,787 B2
(45) Date of Patent: Apr. 15, 2008

(54) GUIDING AND POSITIONING DEVICE AND A SYSTEM FOR POSITIONING A CATHETER WITHIN A VEIN BY MEANS OF THE DEVICE

(75) Inventor: Thomas William Moss, Redditch (GB)

(73) Assignee: Unomedial Limited, Redditch (GB)

( * ) Notice: Subject to any disclaimer, the term of this patent is extended or adjusted under 35 U.S.C. 154(b) by 181 days.

(21) Appl. No.: 11/029,897

(22) Filed: Jan. 5, 2005

(65) Prior Publication Data

US 2005/0148936 A1    Jul. 7, 2005

Related U.S. Application Data

(63) Continuation of application No. PCT/IB2004/004320, filed on Dec. 17, 2004.

(60) Provisional application No. 60/534,539, filed on Jan. 6, 2004.

(30) Foreign Application Priority Data

Dec. 18, 2003 (GB) ................................ 03258023.5

(51) Int. Cl.
*A61M 5/00* (2006.01)
*A61M 5/32* (2006.01)
(52) U.S. Cl. ..................... 604/116; 604/117; 604/174
(58) Field of Classification Search ................. 604/510, 604/116, 117, 164.13, 180, 103.04, 174, 175, 604/179, 197, 198, 263, 110
See application file for complete search history.

(56) References Cited

U.S. PATENT DOCUMENTS 3,467,096 A * 9/1969 Horn ........................ 604/173

| D256,617 | S |   | 8/1980  | Clemens |
|----------|---|---|---------|---------|
| 4,260,077 | A |   | 4/1981  | Schroeder |
| 4,306,562 | A |   | 12/1981 | Osborne |
| 4,332,248 | A |   | 6/1982  | DeVitis |
| 4,497,325 | A | * | 2/1985  | Wedel ..................... 600/567 |
| 4,539,976 | A |   | 9/1985  | Sharpe |
| 4,568,329 | A |   | 2/1986  | Mahurkar |
| 4,626,240 | A |   | 12/1986 | Edelman et al. |
| 4,650,472 | A |   | 3/1987  | Bates |
| 4,655,750 | A |   | 4/1987  | Vaillancourt |
| 4,682,978 | A |   | 7/1987  | Martin |
| 4,808,156 | A |   | 2/1989  | Dean |

(Continued)

*Primary Examiner*—Kevin C. Sirmons
*Assistant Examiner*—Elizabeth MacNeill
(74) *Attorney, Agent, or Firm*—Klein, O'Neill & Singh, LLP; Howard J. Klein

(57) ABSTRACT

A device for positioning a bore needle into a specific position within a vein includes a first body defining proximal and distal ends. A first needle extends from the distal end, establishing fluid communication through the first body from the distal to the proximal end. A second body co-axially supports the bore needle for rotational orientation in the specific position, and has a distal end with an aperture that defines an angle relative to the longitudinal axis of the bore needle. The first and second bodies are respectively mounted to first and second opposed sides of a web body that defines an angle between the first needle and the bore needle when the bore needle is received in the second body, for positioning the aperture of the bore needle in the specific position in alignment with the first needle and opening substantially in the longitudinal direction of the first needle.

16 Claims, 6 Drawing Sheets

U.S. PATENT DOCUMENTS

Figure 1:
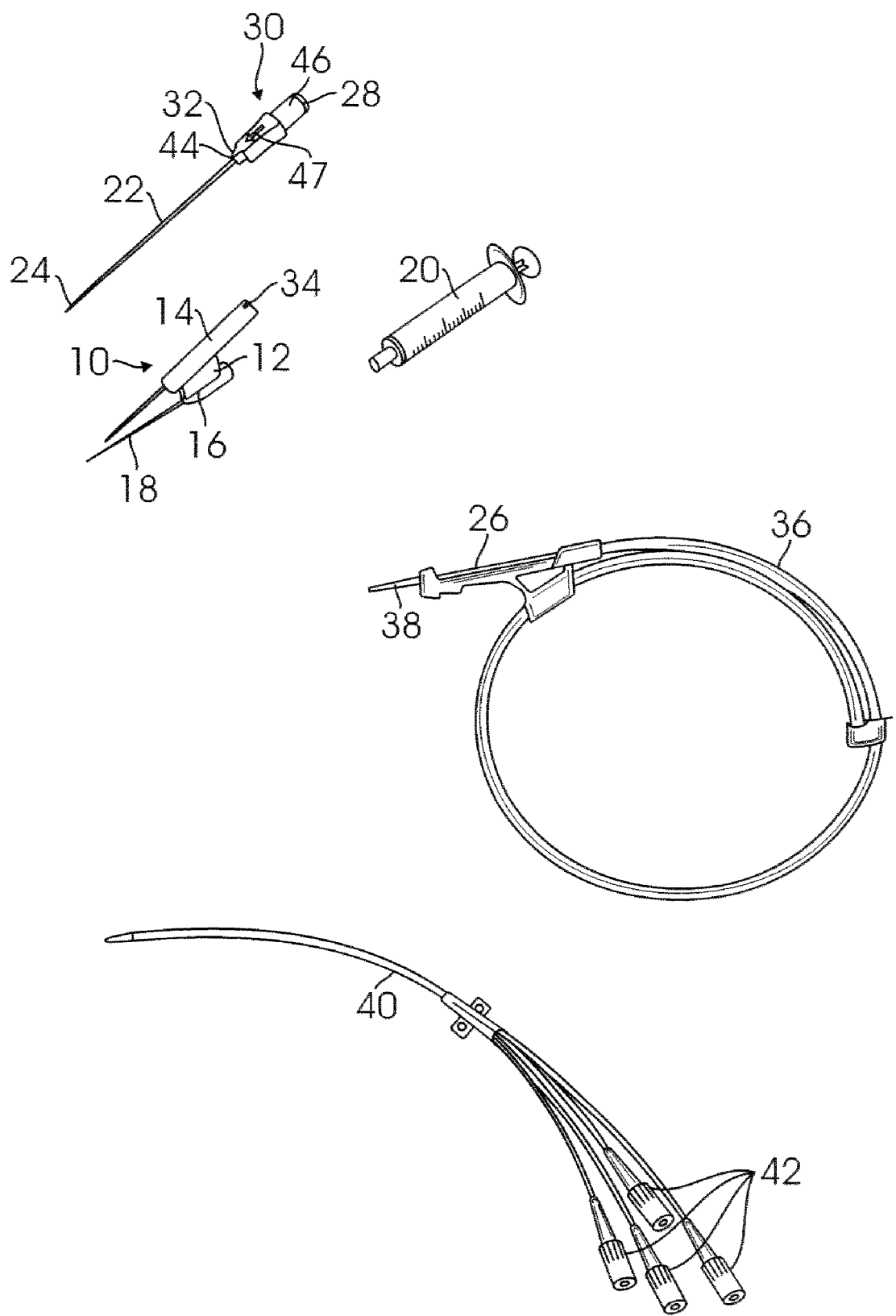

| | | |
|---|---|---|
| 4,834,710 A | 5/1989 | Fleck |
| 4,850,974 A | 7/1989 | Bickelhaupt et al. |
| 4,925,448 A | 5/1990 | Bazaral |
| 5,047,036 A | 9/1991 | Koutrouvelis |
| 5,125,906 A | 6/1992 | Fleck |
| 5,147,314 A | 9/1992 | Vaillancourt |
| 5,235,987 A | 8/1993 | Wolfe |
| 5,263,938 A | 11/1993 | Orr et al. |
| 5,279,573 A | 1/1994 | Klosterman |
| 5,282,479 A | 2/1994 | Havran |
| 5,290,242 A | 3/1994 | Vaillancourt |
| 5,290,244 A * | 3/1994 | Moonka ............... 604/164.13 |
| 5,290,259 A | 3/1994 | Fischer |
| 5,358,495 A | 10/1994 | Lynn |
| 5,366,444 A | 11/1994 | Martin |
| 5,395,317 A | 3/1995 | Kambin |
| 5,454,785 A | 10/1995 | Smith |
| 5,484,419 A | 1/1996 | Fleck |
| 5,507,300 A | 4/1996 | Mukai et al. |
| 5,579,780 A | 12/1996 | Zadini et al. |
| 5,730,150 A | 3/1998 | Peppel et al. |
| 5,733,262 A | 3/1998 | Paul |
| 5,762,629 A | 6/1998 | Kambin |
| 5,827,202 A | 10/1998 | Miraki et al. |
| 5,843,002 A | 12/1998 | Pecor et al. |
| 5,911,707 A | 6/1999 | Wolvek et al. |
| 6,011,988 A | 1/2000 | Lynch et al. |
| 6,053,860 A | 4/2000 | Brooks |
| 6,074,304 A | 6/2000 | Paul |
| 6,086,564 A * | 7/2000 | McLaughlin ............... 604/179 |
| 6,139,540 A | 10/2000 | Rost et al. |
| 6,217,556 B1 | 4/2001 | Ellingson et al. |
| 6,475,190 B2 | 11/2002 | Young |
| 6,477,402 B1 | 11/2002 | Lynch et al. |
| 6,506,182 B2 | 1/2003 | Estabrook et al. |
| 6,537,266 B1 | 3/2003 | Mottola et al. |
| 6,551,281 B1 | 4/2003 | Raulerson et al. |
| 6,572,532 B1 | 6/2003 | Pratt et al. |
| 6,638,242 B2 | 10/2003 | Wilson et al. |

\* cited by examiner

GUIDING AND POSITIONING DEVICE AND A SYSTEM FOR POSITIONING A CATHETER WITHIN A VEIN BY MEANS OF THE DEVICE

CROSS-REFERENCE TO RELATED APPLICATION

This application is a continuation of co-pending International Application No. PCT/IB2004/004320, filed Dec. 17, 2004, the disclosure of which is incorporated herein by reference. This application further claims the benefit, under 35 U.S.C. §119(e), of now abandoned U.S. provisional application no. 60/534,539, filed Jan. 6, 2004, the disclosure of which is incorporated herein by reference.

FEDERALLY-SPONSORED RESEARCH OR DEVELOPMENT

Not Applicable

BACKGROUND OF THE INVENTION

The present invention relates to a device for performing medical procedures, such as internal jugular cannulation. More specifically, the present invention lays according to a first aspect to a guiding and positioning device for guiding and positioning a bore needle into a specific position within a vein of a patient or person.

In medical treatment, a need for implanting or inserting devices such as catheters into the human body, preferably into veins, exist. The catheter may be introduced into the human body by use of a large bore needle inserted into a vein. In order for a health care person to locate a vein in a human body, the health care person may use a small syringe, an ultrasound device or possibly both for locating a suitable vein When the health care person has located the vein, the large bore needle may then be inserted into the vein.

Devices for inserting or introducing needles into the human body have been described in previous publications, such as EP 1 247 541, GB 2,343,845, FR 2,292,457 and U.S. Pat. No. 5,375,588, which are hereby incorporated into the present specification by reference. According to the technique described in the above-mentioned European patent application, a device for guiding the bore needle into the vein of the human body is provided, which device to some extent solves the problems involved in accurately positioning the bore needle within the vein of the human body, as the bore needle is used for the introduction of a guiding wire, which is then used for the guiding of the catheter into the vein after the removal of the bore needle.

The structure known from the above-mentioned European patent application, however, suffers from the drawback that the bore needle may be positioned in an inaccurate orientation, which in the worst case may cause the later introduction of the guiding wire to cause injury to the vein of the patient or person.

An object of the present invention is to provide an improved a universally applicable device for guiding and positioning a bore needle into a specific position within a vein of a patient or person, which device specifically ensures that the bore needle when reaching its intentional position within the vein of the patient or person is properly orientated for allowing a safe and smooth introduction of the guiding wire into the vein of the patient or person in question.

The above object together with numerous other objects, features and advantages, which will be evident from the below detailed description of the presently preferred embodiments of the device for guiding and positioning a bore needle into a specific position with a vein of a patient or person according to a first aspect of the present invention is according to the teachings of the present invention obtained by the guiding and positioning device comprising: a first body defining a proximal end and a distal end and including a first needle extending from said distal end and establishing fluid communication through said first body from said distal end to said proximal end, a second body for co-axially supporting and receiving said bore needle having an aperture at its distal end, said aperture defining a specific angle relative to the longitudinal axis of said bore needle, said second body and said bore needle including positioning means, a web body defining opposite first and second sides, said first body being mounted to said web body at said first side and said second body being mounted to said web body at said second side, respectively, said web body defining an angle between said first needle and said bore needle when received in said second body for positioning said aperture of said bore needle in said specific position in alignment with said first needle and opening substantially in the longitudinal direction of said first needle, and said positioning means rotationally orientating said bore needle in said specific position.

According to the basic teachings of the present invention, the positioning of the bore needle in its intentional orientation within the vein of the patient or person is obtained based on the realisation that the aperture of the bore needle should be positioned substantially opening in the longitudinal direction of the first needle, which needle in its intentional position within the vein is positioned aligned with the vein and at the same time, the aperture of the bore needle is positioned aligned with the first needle and thereby also aligned with the vein of the patient or person. The obtaining of the proper positioning of the aperture of the bore needle which is mandatory as to the prevention of causing any harm or injury to the vein in the guiding wire is introduce into the bore needle is ensured by the provision of the web body interconnecting the first and second device.

The proper positioning of the bore needle having its aperture opening substantially in the longitudinal direction of the first needle may, according to a first and presently preferred embodiment of the guiding and positioning device according to the present invention be obtained by the fulfilment of a specific angular relation between the aperture defining a plane and the longitudinal axis of the first needle. In particular, the aperture defines a plane which further defines an aperture angle with the longitudinal axis of the first needle, which aperture angle preferably is of the order of 75°-160°, such as 90°-135°, preferably approximately 120°, or 75°-80°, 80°-85°, 85°-90°, 90-95°, 95°-100°, 100°-105°, 105°-110°, 110°-115°, 115°-120°, 120°-125°, 125°-130°, 130°-135°, 135°-140°, 140°-145°, 145°-150°, 150°-155° or 155°-160°.

The plane defined by the aperture may be established by the aperture itself provided the aperture is produced by a straight cut through the tubular needle generating an elliptical aperture positioned in a single plane. Provided the aperture is produced by a different cut such as a curved cut, the aperture may not define a single plane, however, in the present context, the plane defined by the aperture is considered defined by the top and bottom point of the closed loop curve defined by the aperture. The angular relation between the plane defined by the aperture of the bore needle and the longitudinal axis of the first needle has to establish an orientation of the aperture of the bore needle as already discussed above, which guides the wire to be introduced into the bore needle into the vein without being orientated towards the wall of the vein in order to prevent that the vein be perforated or injured by the introduction of the wire. Preferably, the wire is introduced in the longitudinal direction of the vein, which direction is corresponding to the longitudinal axis of the first needle, which is in the intentional application of the device according to the present invention positioned extending in the longitudinal direction of the vein.

The first body including at its distal end a first needle serving as a first guide for the positioning of the guiding and positioning device relative to the vein of a patient or person is preferably constituted by a tubular body which extends preferably co-axially with the first needle. Alternatively, the first body may be constituted by a basically U-shaped body, in which the first needle may be received within the groove of the U-shaped body and thereby allowing the first needle to be removed for disposal after use and allowing the positioning device including the first and second bodies and the web body to be sterilised after use.

For ensuring that the first needle is properly positioned within the vein of the patient or person, the first body further preferably comprises at its proximal end, a fitting for receiving a syringe in fluid communication with a first needle, thereby allowing the person using the guiding and positioning device to ensure by the operation of the syringe received within the fitting of the first body by simple suction a small volume of blood from the vein into the syringe, thereby ensuring the proper and intentional positioning of the first needle within the vein of the patient or person.

According to the presently preferred embodiment of the guiding and positioning device according to the first aspect of the present invention, the first needle is fixated to the first body at the distal end thereof, thereby preventing any unintentional loosening of a first needle from the first body of the guiding and positioning device which loosening might result in incorrect operation and malfunction of the device and thereby possibly causing incorrect positioning of the bore needle relative to its intentional position.

Alternatively, the first needle may constitute a separate component and may be connectable through a connector to the first body as already discussed above.

The second body which serves as the guide for the bore needle is like the first needle preferably constituted by a tubular body having at its proximal end a guiding recess for receiving a co-operating protruding part of the bore needle for establishing said positioning means. Alternatively, the positioning means may be constituted by any other appropriate set of elements such as a recess provided at the bore needle and a protruding pin provided at the second body for co-operating with the recess in establishing the positioning means.

Apart from the possibility of switching the various elements of the positioning means between the bore needle and the second body, the positioning means may be provided in a plurality of guiding recesses and said bore needle or said second body having a corresponding plurality of co-operating guiding pins.

It is to be understood that the terms pin and recess are merely examples of elements, which may serve as guiding means, as the pin may be substituted by e.g. a cam or a plate element serving the same purpose as the pin by protruding from the supporting element being the bore needle or in the alternative embodiment, the second body and the recess may be constituted by an aperture, a bore or a similar cavity serving the purpose of receiving the pin, the recess or the plate element etc. All the above elements and similar elements serving the purpose of guiding and properly positioning the bore needle in its intended and proper rotational orientation are to be construed equivalent to the above described pin and recess.

According to a particular feature of the guiding and positioning device according to the first aspect of the present invention, the inner bore of the second body is preferably adapted to receive a bore needle of a specific outer diameter as the second body preferably being a tubular body, is adapted to provide a close guiding of the bore needle, thereby preventing that the outer blunt and apertured end of the bore needle is swagging or otherwise moved from the intentional orientation of motion of the bore needle being identical to the longitudinal axis of the tubular second body.

The proper guiding of the bore needle within the second body is further improved by providing an enlarged part of the bore of the second body at the proximal end thereof for receiving a co-operating enlarged of the bore needle which part also advantageously includes the guiding pin for co-operating with the recess provided at the enlarged bore part of the inner bore of the second body. The larger diameter enlarged part of the bore needle provides an accurate fit of the bore needle within the enlarged inner bore part of the second body, thereby providing the accurate and precise guiding of the bore needle along the longitudinal axis of the second body.

The three main components of the guiding and positioning device according to the first aspect of the present invention may be constituted by separate components which are assembled into a structure by means of e.g. snap fittings, closure elements, such as bolts and knots etc.

Provided the guiding and positioning device be assembled from separate elements, the first or alternatively second body may be rotatably mounted relative to the web body for allowing the device to be adjusted to alternative lengths of bore needles, thereby making the device universally applicable.

According to the presently preferred embodiment of the guiding and positioning device according to the first aspect of the present invention, the first body, the second body and the web body are constituted by an integral structure cast from preferably one and the same plastics material.

For ensuring a proper guiding of the bore needle within the second device by the provision of the enlarged inner bore part of the second body at the proximal end thereof, the enlarged inner bore preferably constitutes at least 5% of the length of the second body, such as 5-100%, preferably 10-85%, further preferably 10-50% of said bore, or alternatively constituting 5-10%, 10-15%, 15-20%, 20-25%, 25-30%, 30-35%, 35-40%, 40-45%, 45-50%, 50-55%, 55-60%, 60-65%, 65-70%, 70-75%, 75-80%, 80-85%, 85-90%, 90-95% or 95-100%.

Further, for ensuring the proper guiding of the bore needle within the bore of the second body, the enlarged diameter bore preferably constitutes at least an enlargement of the through-going bore of 200% such as an enlargement of 200-1000%, preferably 300-800%, further preferably 500-700%, or alternatively constituting an enlargement of 200-300%, 300-400%, 400-500%, 500-600%, 600-700%, 700-800%, 800-900%, 900-1000%.

The guiding and positioning device may be made from any appropriate preferably non-bendable material capable of providing an accurate and precise guiding of the bore needle into its intentional position. Examples relevant and advantageous materials are hard plastics materials such as ABS, POM or alternatively stainless steel.

The above object together with numerous other objects, advantages and features which will be evident from the below detailed description of the preferably preferred embodiments of the present invention are according to a second aspect of the present invention obtained by a system for positioning a catheter within a vein of a patient or person, which system comprises the catheter, a guiding wire, a bore needle and a guiding and positioning device comprising: a first body defining a proximal end and a distal end and including a first needle extending from said distal end and establishing fluid communication through said first body from said distal end to said proximal end, a second body for co-axially supporting and receiving said bore needle having an aperture at its distal end, said aperture defining a specific angle relative to the longitudinal axis of said bore needle, said second body and said bore needle including positioning means, a web body defining opposite first and second sides, said first body being mounted to said web body at said first side and said second body being mounted to said web body at said second side, respectively, said web body defining an angle between said first needle and said bore needle when received in said second body, an angle for positioning said aperture of said bore needle in said specific position in alignment with said first needle and orientated substantially perpendicular to the longitudinal axis of said first needle, and said positioning means rotationally orientating said bore needle in said specific position, said bore needle serving for guiding said wire into said vein and said wire serving for threading and guiding said catheter into said vein of said patient or person.

The system for positioning a catheter within a vein of a patient or person generally comprises the guiding and positioning devices according to the first aspect of the present invention and further the wire and the bore needle together with the catheter itself.

The guiding wire may be made from any relevant material such as a plastics wire or plastics line, however, the guiding wire is preferably made as a threaded or woven stainless steel wire.

The catheter of the system according to the second aspect of the present invention may be constituted by a single tubular catheter or alternatively comprise a plurality of catheter entry fittings as is well known in the art per se.

The above object together with numerous other objects, features and advantages, which will be evident from the below detailed description of the presently preferred embodiments of the device for guiding and positioning a bore needle into a specific position with a vein of a patient or person according to the third aspect of the present invention is according to the teachings of the present invention obtained by a method of positioning a catheter within a vein of a patient or person, the method comprising: providing a guiding and positioning device and a bore needle, said guiding and positioning device serving for guiding and positioning said bore needle into a specific position within said vein of said patient or person, said guiding and positioning device comprising: a first body defining a proximal end and a distal end and including a first needle extending from said distal end and establishing fluid communication through said first body from said distal end to said proximal end, a second body for co-axially supporting and receiving said bore needle having an aperture at its distal end, said aperture defining a specific angle relative to the longitudinal axis of said bore needle, said second body and said bore needle including positioning means, a web body defining opposite first and second sides, said first body being mounted to said web body at said first side and said second body being mounted to said web body at said second side, respectively, said web body defining an angle between said first needle and said bore needle when received in said second body, an angle for positioning said aperture of said bore needle in said specific position in alignment with said first needle and orientated substantially perpendicular to the longitudinal axis of said first needle, and said positioning means rotationally orientating said bore needle in said specific position, the method further comprising providing a guiding wire and said catheter, and comprising the step of positioning said bore needle in said specific position by means of said guiding and positioning device, guiding said guiding wire through said bore needle into said specific position within said vein of said patient or person, removing said bore needle from said specific position within said vein of said patient or person and leaving said guiding wire in said position within said vein, removing said guiding and positioning device, threading said catheter onto said guiding wire and positioning said catheter in said specific position within said vein of said patient or person, removing said guiding wire and fixating said catheter to the skin surface of said patient or person by means of a fixating tape.

The present invention will now be further described in detail with reference to the figures, wherein:

FIG. 1 is a diagrammatic view of items used when performing internal jugular cannulation, FIGS. 2a-2e schematically illustrates alternative embodiments of bore needles, FIGS. 3-8 are schematic illustrations of alternative embodiments of the needle guide, and FIGS. 9-19 schematically illustrate the operations performed by a health care person when applying a drainage tube or catheter.

DETALED DESCRIPTION OF THE INVENTION

FIG. 1 is a diagrammatic view of items used when performing internal jugular cannulation, especially a needle guide 10 according to the present invention. The needle guide 10 comprises a central body 12 connecting a bore needle guide tube 14 and a connector piece 16. A needle 18 is mounted in connection with the connector piece 16 such that a fluid may pass from the tip of the needle to the opposite end of the connector piece 16. The connector piece 16 is adapted for receiving a suction device such as a syringe 20. The bore needle guide 14 is adapted for receiving a large bore needle 22. The bore needle 22 has an angled aperture 24 at the tip for guiding a wire 26 from an opening 28 of the bore needle to a predefined location such as within a vein in a human body.

Previously, health care persons such as doctors or nurses passing catheters into veins of a patient, used a large bore needle for locating a suitable vein, e.g. a vein in the hand or neck area of a patient. Irrespective of the skill of the health care person performing the introduction of the large bore needle, the health care person is bound to make mistakes and consequently inflicting pain and/or unnecessary damage to a patient's skin.

A health care person using the needle guide according to the present invention uses the needle 18 for locating a suitable vein in the patient. The health care person then utilises the syringe 20 to aspirate for detecting the correct placement of the needle 18 in a blood vein of the patient. The health care person, who has now established a safe entry point for the catheter, inserts the bore needle 22 through the opening of the bore needle guide tube 14.

The bore needle guide tube 14 forms an angle with the connector piece 16 such that a bore needle passed through the bore needle guide tube 14 is inserted into the patient as close as possible to the tip of the needle 18 and in a specific intentional orientation. The health care person inserting the bore needle 22 using the present invention is certain that the large bore needle 22 only needs to be inserted or introduced into the patient once.

The angle defined by an axis through the bore needle guide tube 14 and a second axis through the connector piece 16 along with the length of the needle 18 determines the preferred length of the large bore needle 22.

In the presently preferred embodiment of the present invention, the bore needle guide tube 14 is fixed relative to the connector piece 16, also the length of the needle 18 is fixed. The geometry of these fixed items allows for only one length of the large bore needle 22.

In alternative embodiments, a bore needle guide tube 14 being mounted pivotally to the central body 12 may be envisioned. Further alternatively, an embodiment having a replaceable bore needle guide tube 14 may be envisioned, i.e. for the support of a plurality of bore needles all having different diameters. Still further alternatively an embodiment of the present invention wherein the tubular bore needle guide 14 and the central body 12 constitutes a device that may be attachable to a syringe and after use may be detached therefrom. This embodiment allows for reduction of the amount of material used and a larger variety of syringes may be used.

When introducing a wire 26 into the human body using the presently preferred embodiment of the present invention, it is crucial that the angled aperture 24 of the bore needle 22 is orientated such that the wire 26 exiting the angled aperture 24 in a direction substantially parallel to the needle 18.

In order to ensure that the angled aperture 24 is orientated correctly, the bore needle 22 is provided with a grip 30, wherein a protruding rib 32 is formed. The protruding rib 32 extends parallel to the needle 18.

A groove 34 corresponding to the protruding rib 32 is formed in the bore needle guide tube 14 for locking the bore needle 22 in a fixed orientation prior to the bore needle 22 breaking the patient's skin. In an alternative embodiment of the device according to the present invention the bore needle guide tube 14 may include a protruding rib for the fixation of the bore needle, and a corresponding groove may be formed in the handle 30.

FIG. 1 further illustrates the wire 26 encased in a jacket 36 and having a tip 38 for guiding the wire 26 into the opening 28 of the grip 30. The wire illustrated in FIG. 1 with corresponding jacket 36 is a commercial product available from Unomedical. Other commercially available wires may of course be used in connection with the needle guide 10.

The handle 30 may be extended by an elongated sleeve or jacket 44 whereupon the rib 32 may be placed or formed.

FIG. 1 further illustrates a central vein catheter 40 that is to be inserted into the vein of a patient. The central vein catheter 40 comprises a plurality of adapters or fitting 42 for injecting fluids into the vein of the patient, e.g. a salt water solution, analgesics, anti-bacterial medication or any other medical treatment available in a fluid solution. The needle guide 10 according to the present invention may also be used in connection with application of drainage tubes.

The handle 30 includes an arrow 47 for visually indicating to the health care person that the angled aperture 24 is orientated correctly.

The opening 28 illustrated throughout the FIGS. 1-16 all have circular cross sections and are illustrated having a tubular part 46, however, embodiments where at least part of the tubular part 46 includes a gradual enlargement of the diameter, e.g. similar to that of a funnel, may be envisioned for facilitating the insertion of a wire into the opening 28.

Figure 2A:
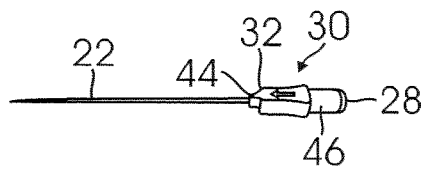

FIG. 2a illustrates a bore needle 22 and a grip 30 extended by a sleeve or jacket 44 to be received in a corresponding aperture adapted for fixating the bore needle prior to inserting the bore needle 22 in the patient's skin. The jacket or sleeve 42 increases stability and precision of the bore needle 22 and the protruding rib 32 ensures that the bore needle is inserted into the patient with the angled aperture 24 orientated such that the angled aperture 24 allows a wire to exit the bore needle in a direction substantially parallel to the needle 18, thereby the wire is able to enter the vein of the patient without causing damage to the inside of the vein.

The bore needle guide tube 14 includes a through-going hole adapted for receiving the bore needle 22. In the presently preferred embodiment of the present invention, the through-going hole of the bore needle guide tube 14 has a diameter substantially corresponding to the outer diameter of the bore needle 22 such that the bore needle 22 is firmly guided through the bore needle guide tube 14 without wobble. The inside of the through-going hole may be reinforced by a metallic tube or a metallic layer deposited thereon to ensure that no plastic is shredded from the inside of the tubular guide 14 by the bore needle and introduced into the vein of the person or patient.

Figure 2B:
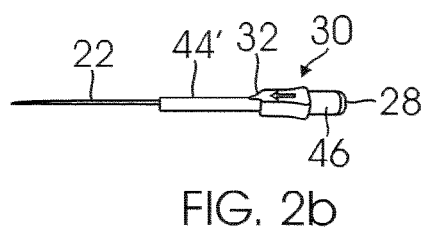

FIG. 2b illustrates an alternative embodiment of the guiding means constituted by an elongated sleeve or jacket 44' as compared with the jacket or sleeve 44 illustrated in FIG. 2a. The elongated sleeve or jacket 44' requires that the bore needle guide tube 14 be adapted for receiving the elongated jacket or sleeve 44'. The elongated jacket or sleeve 44' enables the employment of a plurality of bore needles having different diameters for a variety of uses. Thereby, the through-going hole of the bore needle guide tube 14 may have a large inner diameter for the support of a plurality of bore needles having different diameters, thereby the need for a tight fitting around the bore needle 22 is no longer required as the tight guiding of the bore needle is performed by the elongated sleeve 44'. The protruding rib 32 in this embodiment enables a rotational fixation of the bore needle relative to the bore needle guide tube 14.

Figure 2C:
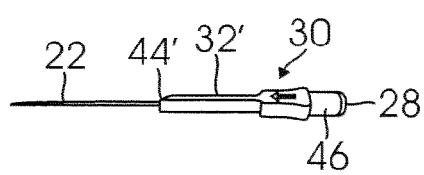

FIG. 2c illustrates an embodiment similar to that of FIG. 2b, wherein the protruding rib 32 has been elongated in a radial direction illustrated by the protruding rib 32'. This enables a rotational fixation of the bore needle at an earlier stage when inserting the bore needle into the bore needle guide tube 14, thereby ensuring that angled tip 24 is fixated at the correct angle relative to the skin surface of a patient and no rotation is required after the insertion of the bore needle tip 24 in the skin surface part of a patient.

Figure 2D:
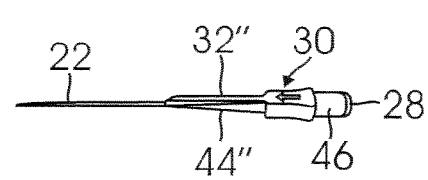
Figure 2E:
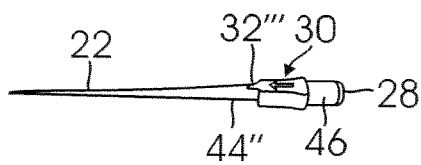

FIGS. 2d and 2e illustrate an embodiment of the bore needle including a jacket or sleeve 44" having a conical or tapered geometric configuration. Also the protruding rib 32" and 32"' have been adapted and illustrating two different lengths in the radial direction of the protruding rib. The protruding rib as illustrated in the FIGS. 2a-2e may of course have many other length than indicated in the drawings.

The sleeves or jackets illustrated in FIGS. 2a-2e all have circular cross sections, however, other cross sections might be envisioned, such as elliptical, triangular, square, rectangular, pentagonal, hexagonal, heptagonal or any geometric variation or combination thereof. A Jacket or sleeve enclosing a part of the bore needle having a cross section other than circular may be advantageous as to fixating the angled aperture of the bore needle relative to the skin surface part of a patient. An elliptical cross section of the jacket or sleeve will e.g. only allow two possible orientations of the angled aperture and a protruding rib may be added to ensure that the correct orientation is selected by the health care person. Also a plurality of ribs, tongues, cams or edges may constitute the guiding means, and corresponding receiving grooves may be added.

Figure 3:
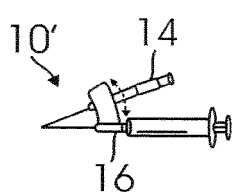

FIG. 3 is a schematic side view of an alternative embodiment of the needle guide 10', wherein the bore needle guide 14 may be displaced or shifted relative to the connector piece 16. The bore needle guide 14 may then be shifted or displaced in order to obtain a more favourable entry angle into the skin surface of the patient.

The tubular bore needle guide in the embodiment illustrated in FIG. 3 revolves around the point of intersection between the bore needle tip 24 and the tip of the needle 18, however, embodiments wherein the bore needle guide tube 14 may be displaced vertically and at the same time may be pivoted for the support of a plurality of bore needles having different lengths and/or different diameters.

Figure 4:
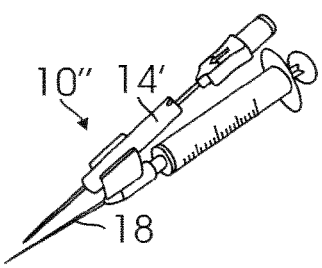

FIG. 4 is a diagrammatic perspective view of an embodiment of the present invention, wherein a tubular bore needle guide tube 14' may be replaceable for the support of a variety or plurality of bore needles, each having a unique diameter. The inner construction of the tubular bore needle guide tube 14' is similar to that of the bore needle guide 14 illustrated in FIG. 1 in that the diameter of the through-going hole is such that the inner walls of the through-going hole guides and supports the bore needle such that wobbling and consequently inaccurate placement of the bore needle in the patient's skin is avoided, also unwanted movement of the bore needle relative to the entry point in the patient's skin is avoided. The embodiment illustrated in FIG. 4 and also in FIG. 5 may be combined with the embodiment illustrated in FIG. 3, whereby multiple orientations of the bore needle guide 14' may be obtained dependent on the situation, wherein the device 10" is used.

Figure 5:
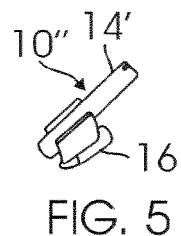

As illustrated in FIG. 5, the needle may be detached from the connecting body 16 and replaced with a needle being either shorter or longer, alternatively having a different diameter or any combinations thereof, depending on the situation, wherein the device is used. It is obvious that this feature, where the needle is detachable from the device 10", may be combined with the embodiments illustrated in the other figures.

In a further alternative embodiment not illustrated, a tubular bore needle guide with a connecting or central body adapted or being attached to a syringe either by being attached at a part of the syringe or having an adapter for receiving the syringe, whereby the needle is associated directly with the syringe and therefore, cleaning of the needle along with the device 10, 10', 10" is not needed.

Figure 6:
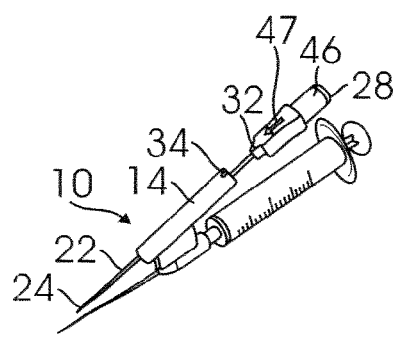

FIG. 6 is a schematic perspective view of an assembly comprising the needle guide 10 with the bore needle 22 inserted into the tubular bore needle guide tube 14. The arrow 47 visually indicates to the health care person performing the internal jugular cannulation whether the angular aperture 24 of the bore needle 22 is orientated correctly, in the correct configuration the arrow points at the groove 34 so that the protruding rib 32 may be received within the groove 34.

Figure 7:
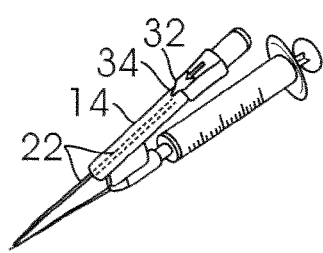
Figure 8:
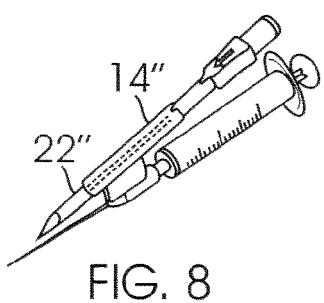

FIG. 7 is a schematic view similar to that of FIG. 6, wherein the bore needle has been received and fully inserted into the skin of a patient indicated by the protruding rib 32 being fully received within the groove 34. The stippled line indicates where the bore needle 22 is located within the tubular bore needle guide 14. FIG. 8 is a schematically perspective view of an embodiment of the tubular bore needle guide 14" adapted for receiving a bore needle 22" having a very large diameter.

FIGS. 9-16 illustrates the steps performed by the health care person when using the present invention, i.e. the needle guide 10, for introducing or entering a catheter into the neck area of a patient. In the present context it is to be understood that the present invention may be used in connection with application or insertion of catheters, drainage tubes or the like in a patient's neck area, arms, arm pit areas, groin, hands or other body parts of a human or animal.

Figure 9:
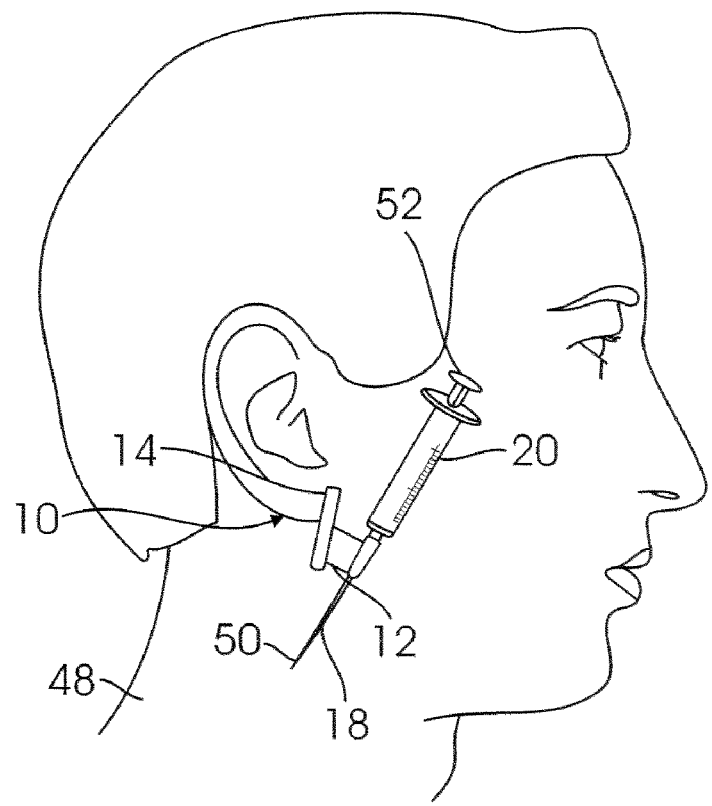

FIG. 9 illustrates the situation where a health care person has inserted the needle 18 into the skin surface of a patient's neck 48, preferably into a vein 50. For detecting whether or not the health care person has in fact identified and inserted the needle 18 into a vein 50, the health care person pulls the plunger 52 in order to visually inspect the chamber of the syringe 20 to see if the syringe 20 is filled with blood In the illustrations, the needle guide 10 is illustrated used on a neck of a patient, however the use is not limited to perform medical tasks on the patient's neck, the needle guide may also be used when performing cannulation or other medical procedures in a patient's neck area, arms, groin or other body parts, where drainage tubes or catheters are to be inserted. Also the device may be used when performing these types of operations or tasks on animals.

Figure 10:
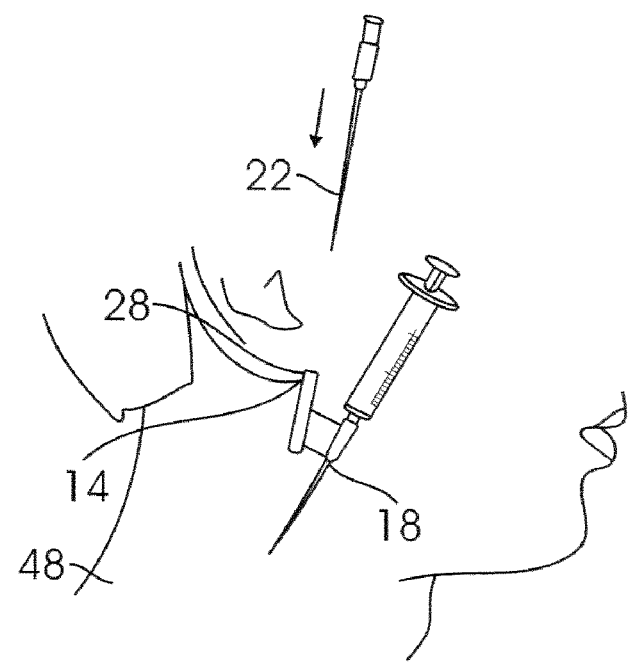

After the health care person has detected and verified the correct insertion of the needle 18 into the patient, the bore needle 22 is inserted into the tubular bore needle guide 14 as illustrated in FIG. 10.

Figure 11:
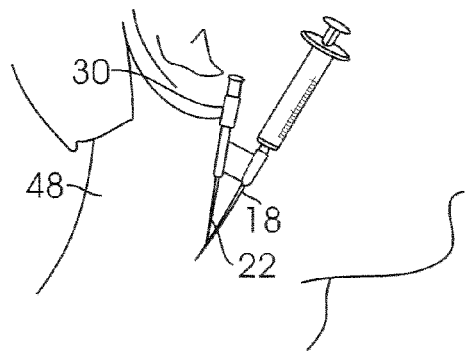
Figure 12:
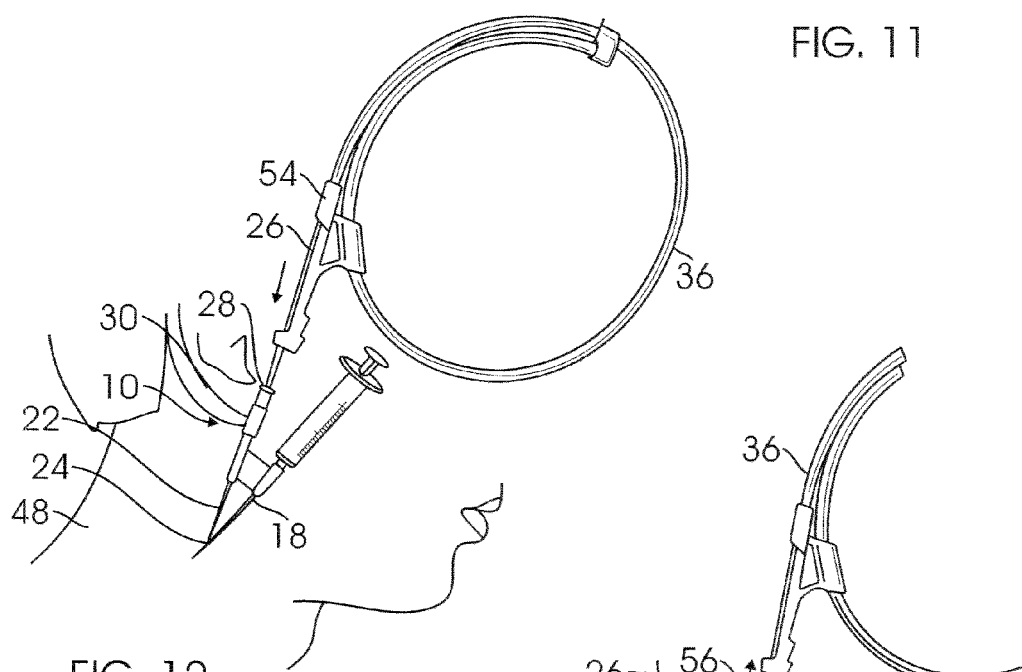
Figure 13:
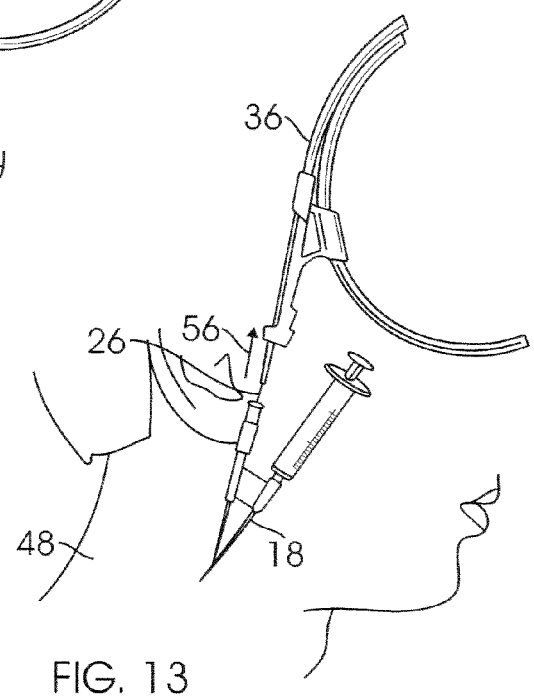
Figure 14:
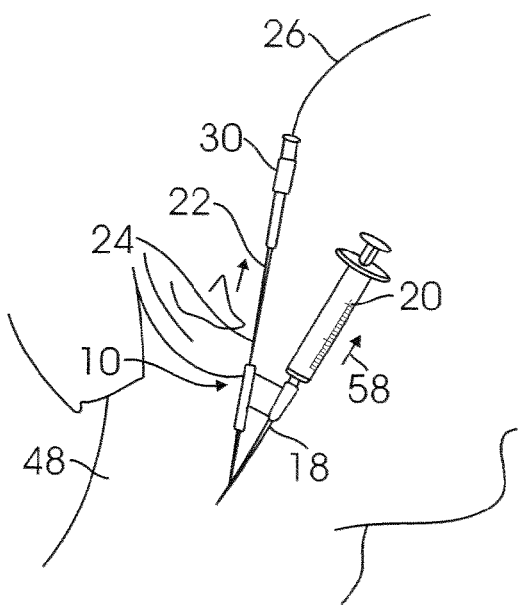

FIG. 11 illustrates the full insertion of the bore needle into the skin of a patient's neck 48, the bore needle 22 is now inserted into the blood vein of the patient and the protruding rib of the bore needle handle or grip 30 ensures that the angled tip of the bore needle 22 is orientated correctly.

A wire 26 is inserted into the opening 28 of the grip 30 so as to be guided into the blood vein of the patient's neck 48. The correct placement of the bore needle 22 is essential to avoid any damage caused by an incorrect placement of the angled tip 24. The wire 26 may be embedded or enclosed in a jacket so as to maintain an antiseptic or bacteria free storage of the wire. The jacket 36 may include a handle 54 and a tip 38 for facilitating the insertion of the wire 26 into the opening 28. Also this guide may allow a health care person to insert the wire while holding the needle guide 10 so as to avoid that the angled aperture 24 of the bore needle 22 is moved.

After inserting the wire 26 into the desired location of the blood vein in the neck 48 of the patient, the jacket 36 may be pulled back as indicated by the arrow 56. The wire is now embedded partly into the blood vein of the patient.

Figure 15:
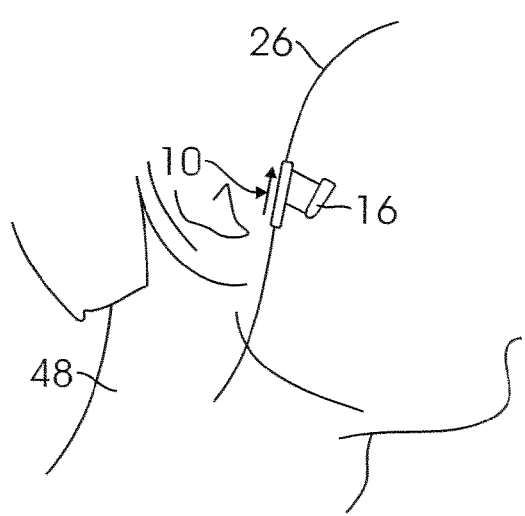
Figure 16:
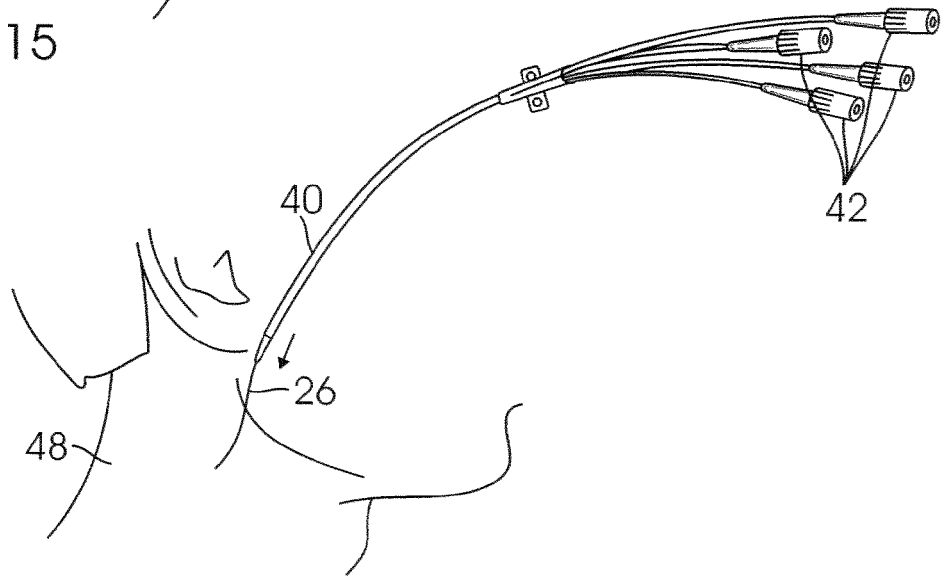
Figure 17:
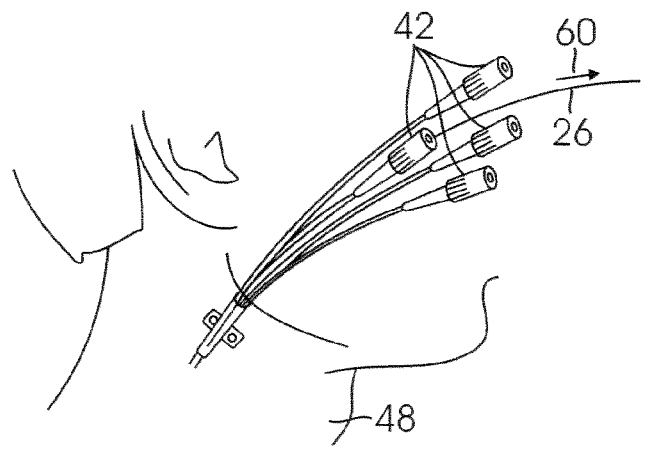

After the removal of the jacket 36, the bore needle 22 may be pulled out from the patient's neck 48 by pulling the grip 30, thereby removing the bore needle 22 from the patient's neck 48 without causing damage to the neck 48. The bore needle 22 is simply removed from the wire by pulling the handle 30 until the wire has exited the angle tip 24. After removing the bore needle 22, the needle guide may be removed from the entry point 10 of the patient's neck 48 by pulling the syringe and/or the needle guide 10 in the direction indicated by the arrow 58. FIG. 15 illustrates how to remove the needle guide 10 provided the syringe 20 is detachable from the needle guide 10, e.g. by inserting the syringe into the connector piece 16. The needle guide 10 is then removed by pulling the needle guide 10 to the end of the wire.

After removing the needle guide 1 0, the health care person then applies a suitable catheter or drainage to the end of the wire and pulls the drainage tube or catheter 40 so as to insert the tip of the catheter 40 into the blood vein and guiding it safely to its target location.

When the drainage tube or catheter 40 has been placed correctly into the blood vein, the wire 26 is pulled through the catheter 40 through a adapter or access tube 42 of the drainage tube or catheter 40 in the direction indicated by the arrow 60.

Figure 18:
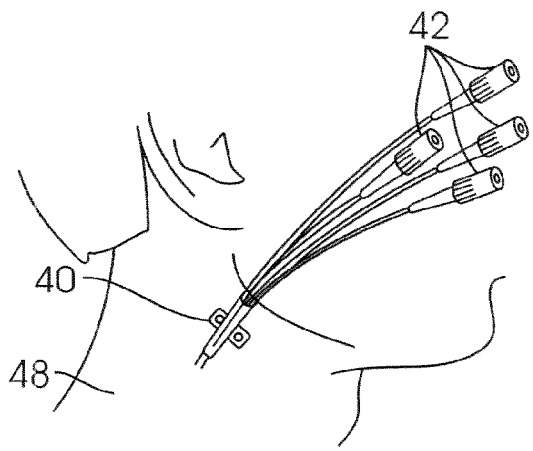
Figure 19:
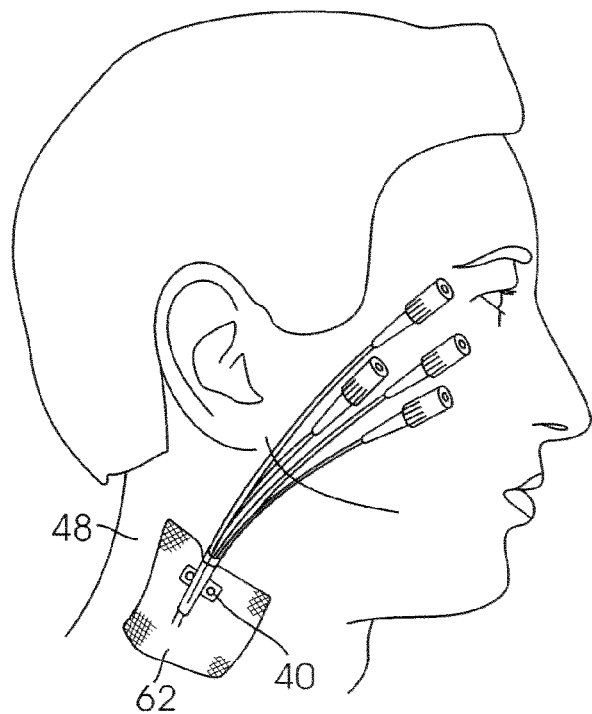

FIG. 18 now illustrates the correct placement of the catheter 40 in the patient's neck 48.

After the correct insertion of the catheter 40, the catheter 40 may be fixated relative to the skin surface of the neck 48 to ensure that the drainage tube or catheter 40 is not moved and thereby causing unnecessary damage to the skin of the neck 48. The fixation may be achieved by applying a large plaster component such as a specialised catheter plaster component 62, such plaster components are commercially available, e.g. from Unomedical under the product name UNO. Alternatively, the fixation may be achieved by simply applying two strips of a suitable material applied with an adhesive, alternatively by a single large plaster component covering the main parts of the drainage tube 40.

The selection of the fixation depends on the duration in which the drainage tube or catheter 40 is to be embedded into the patient. Should the patient wear the catheter 40 for a long period of time, the specialised plaster component is preferably chosen, however, if the drainage tube or catheter is only to be applied, e.g. during a short operation, a simpler and/or cheaper fixation method may be used.

EXAMPLE

A prototype version of the guiding and positioning device according to the present invention has been constructed from the following components:

The first and second tubular bodies were cast from ABS in a unitary structure with the web interconnecting the tubular bodies.

The needle had a total length of 40 mm and a diameter of approximately 0.6 mm. The needle was integrated in the first tubular body. The first tubular body had an opening with a diameter of approximately 4.3 mm.

The bore needle had a length of 70 mm and a diameter of approximately 1 mm. The outer diameter of the opening in the handle of the bore needle was 6.725 mm. The through-going hole had a diameter of 1.6 mm.

The angle defined by the first and second tubular bodies was approximately 20 degrees.

The syringe had a volume of 5 ml.

The invention claimed is:

1. A guiding and positioning device for guiding and positioning a bore needle into a specific position within a vein of a patient or person, the device comprising:
   a web body defining first and second non-parallel opposite sides;
   a first body fixed to the first side of the web body;
   a first needle defining a distal end configured for entering the vein of the patient or person, and a proximal end fixed to the first body, said first needle being configured to provide fluid communication from the vein to the first body;
   a second body fixed to the second side of the web body and configured for co-axially receiving and supporting the bore needle, said second body and said bore needle including positioning means for orienting the bore needle in a fixed rotational position in the second body, said second body defining a first angle between the first needle and the bore needle when said bore needle is received in the second body, the vertex of said first angle being defined by the distal end of the first needle and the distal end of the bore needle, whereby both the first needle and the bore needle, for any value of the first angle, enter the vein of the patient in said specific position; and
   an aperture at the distal end of the bore needle defining a second angle relative to the longitudinal axis of the bore needle, said aperture opening substantially in the longitudinal direction of the first needle when the bore needle is received in the second body.

2. The guiding and positioning device according to claim 1, said aperture defining a plane, said plane defining an aperture angle with the longitudinal axis of said first needle, said aperture angle being of the order of 75°-160°.

3. The guiding and positioning device according to claim 1, said first body being a tubular body.

4. The guiding and positioning device according to claim 1, said first body further comprising at its proximal end a fitting for receiving a syringe in fluid communication with said first needle.

5. The guiding and positioning device according to claim 1, said first needle being fixed to said first body at said distal end thereof.

6. The guiding and positioning device according to claim 1, said first needle constituting a separate component connectable through a connector to said first body.

7. The guiding and positioning device according to claim 1, said second body being a tubular body having at its proximal end a guiding recess for receiving a co-operating protruding part of said bore needle for establishing said specific position.

8. The guiding and positioning device according to claim 7, said second body having an inner bore for receiving a bore needle of a specific outer diameter.

9. The guiding and positioning device according to claim 8, said inner bore being dimensioned for receiving a co-operating part of said bore needle also including said protruding part.

10. The guiding and positioning device according to claim 1, said first body and said second body constituting separate components relative to said web body.

11. A guiding and positioning device according to claim 1, said first body, said second body and said web body constituted by an integral structure.

12. The guiding and positioning device according to claim 1, at least part of said device being made from a material selected from the group consisting of at least one of a hard plastic and stainless steel.

13. A system for positioning a catheter within a vein of a patient or person, said system comprising said catheter, a guiding wire, a bore needle and a guiding and positioning device operable for guiding and positioning said bore needle into a specific position within the vein of said patient or person, said guiding and positioning device comprising:
   a web body having first and second opposite sides;
   a first body fixed to the first side of the web body and defining a proximal end and a distal end and including a first needle extending from said distal end and establishing fluid communication through said first body from said distal end to said proximal end;
   a second body immovably fixed to the second side of the web body and configured for co-axially supporting and receiving said bore needle, said bore needle having an aperture at its distal end, said aperture defining a first specific angle relative to the longitudinal axis of said bore needle, said second body and said bore needle including positioning means; and said web body defining a second specific angle between said first needle and said bore needle when said bore needle is received in said second body for positioning said aperture of said bore needle in said specific position in alignment with said first needle and opening substantially in the longitudinal direction of said first needle;

wherein said positioning means rotationally orients said bore needle in said second body to fix the bore needle in said specific position, said bore needle configured for guiding said wire into said vein and said wire configured for threading and guiding said catheter into said vein of said patient or person.

14. The system according to claim 13, said guiding wire being made from a material selected from the group consisting of at least one of plastic and metal.

15. The guiding and positioning device according to claim 13, said catheter comprising a plurality of catheter entry fittings.

16. A method of positioning a catheter within a vein of a patient or person, said method comprising:

providing a guiding and positioning device and a bore needle, said guiding and positioning device being operable for guiding and positioning said bore needle into a specific position within said vein of said patient or person, said guiding and positioning device comprising:

a web body having opposite first and second sides;

a first body fixed to the first side of the web body and defining a proximal end and a distal end and including a first needle extending from said distal end and establishing fluid communication through said first body from said distal end to said proximal end; and a second body immovably fixed to the second side of the web body and configured for co-axially supporting and receiving said bore needle, said bore needle having an aperture at its distal end, said aperture defining a first specific angle relative to the longitudinal axis of said bore needle, said second body and said bore needle including positioning means;

said web body defining a second specific angle between said first needle and said bore needle when said bore needle is received in said second body for positioning said aperture of said bore needle in said specific position in alignment with said first needle and opening substantially in the longitudinal direction of said first needle;

wherein said positioning means rotationally orients said bore needle in said second body to fix the bore needle in said specific position;

the method further comprising providing a guiding wire and said catheter, and comprising the steps of positioning said bore needle in said specific position by means of said guiding and positioning device, guiding said guiding wire through said bore needle into said specific position within said vein of said patient or person.

removing said bore needle from said specific position within said vein of said patient or person and leaving said guiding wire in said position within said vein, removing said guiding and positioning device, threading said catheter onto said guiding wire and positioning said catheter in said specific position within said vein of said patient or person, removing said guiding wire, and taping said catheter to the skin surface of said patient or person.

\* \* \* \* \*